United States Patent [19]

Talalay

[11] Patent Number: 5,209,739
[45] Date of Patent: May 11, 1993

[54] HYPODERMIC NEEDLE

[76] Inventor: Leon Talalay, 1 Chestnut La., Woodbridge, Conn. 06525

[21] Appl. No.: 903,038

[22] Filed: Jun. 23, 1992

[51] Int. Cl.$^5$ ................................................ A61M 5/00
[52] U.S. Cl. ....................................... 604/195; 604/198
[58] Field of Search ............... 604/195, 198, 110, 187, 604/263; 128/763-765

[56] References Cited

U.S. PATENT DOCUMENTS

| | | | |
|---|---|---|---|
| 4,838,869 | 6/1989 | Allard | 604/198 X |
| 4,874,382 | 10/1989 | Lindemann et al. | 604/195 |
| 5,026,354 | 6/1991 | Kocses | 604/195 |
| 5,084,029 | 1/1992 | Taguaferri et al. | 604/198 X |

Primary Examiner—John D. Yasko
Attorney, Agent, or Firm—Robert H. Montgomery

[57] ABSTRACT

A hypodermic needle assembly comprising a tubular barrel member, a cannula extending from the barrel member, an elastomeric tube connected between the cannula and a fitting at the distal end of the barrel member providing a fluid passage therebetween, the tube being stressed along its length between the cannula and the fitting, releasable means holding the elastomeric tube in a stressed state and means for releasing the cannula from the state in which the tube is stressed such that the elastomeric tube retracts the cannula with sufficient force to pull the cannula out of the patient and place it in a protected position within the barrel. Also disclosed is a structure in which the invention is embodied in a complete hypodermic syringe. Further disclosed is a hypodermic needle assembly in which the invention is adapted for the drawing of blood or other body fluids into an evacuated collection vessel.

24 Claims, 6 Drawing Sheets

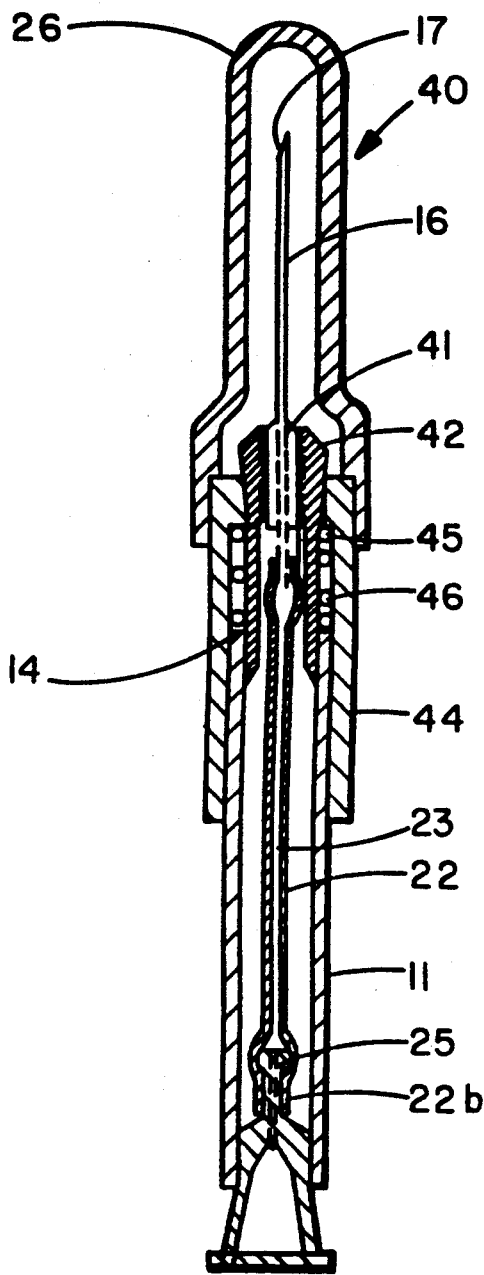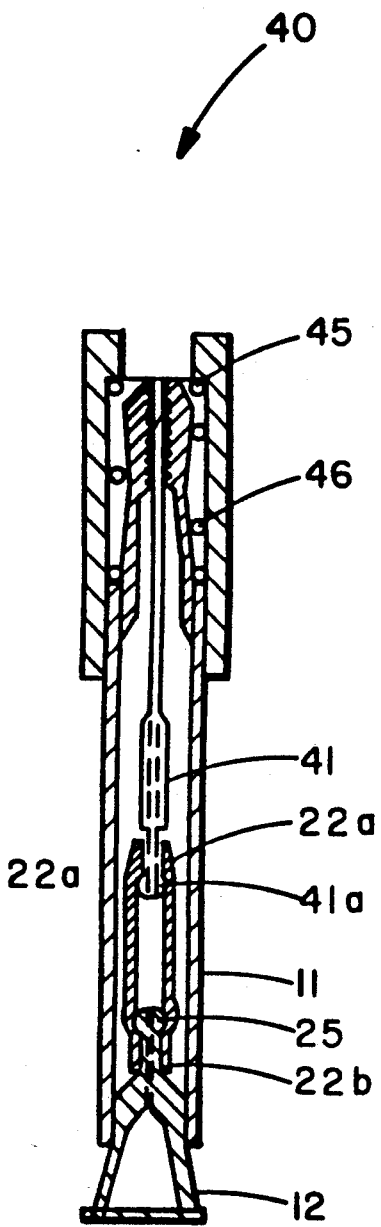
FIG. 2a FIG. 2b

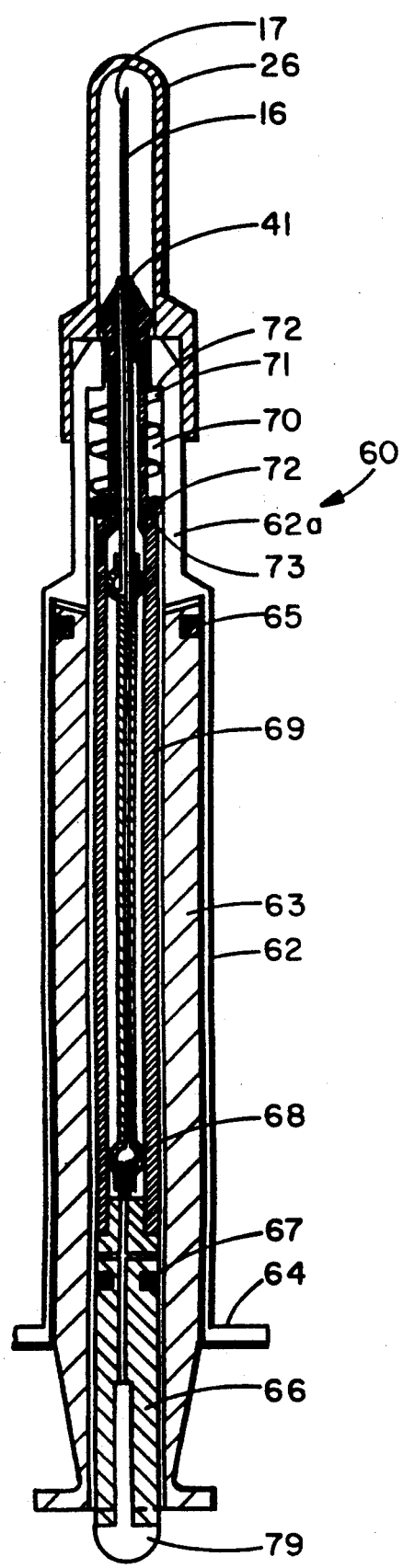
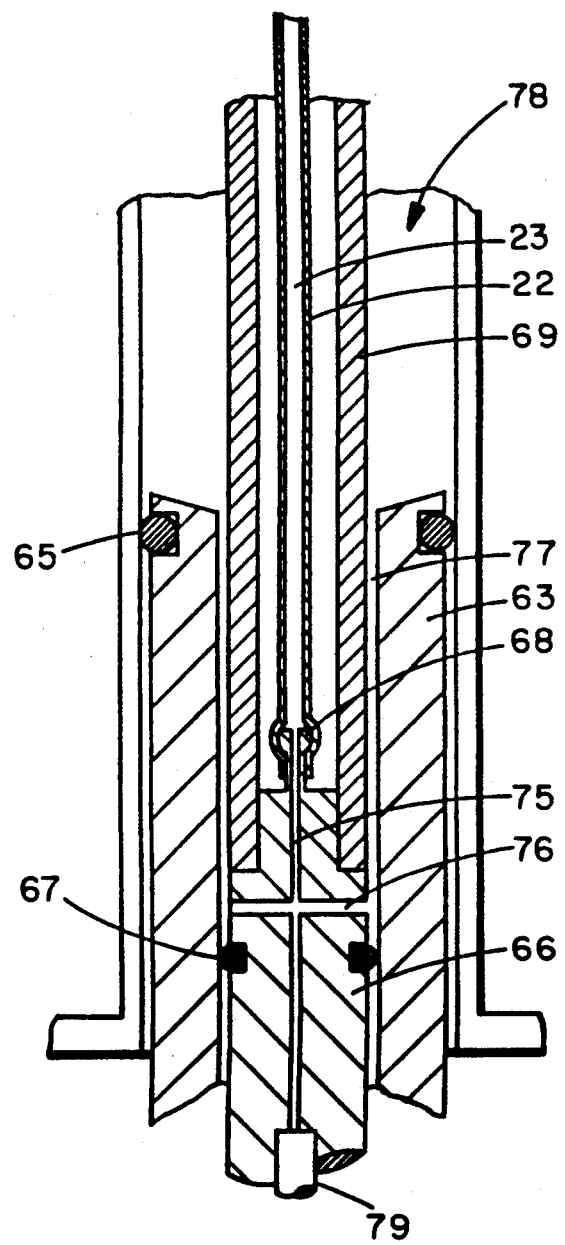
FIG. 4
FIG. 4a

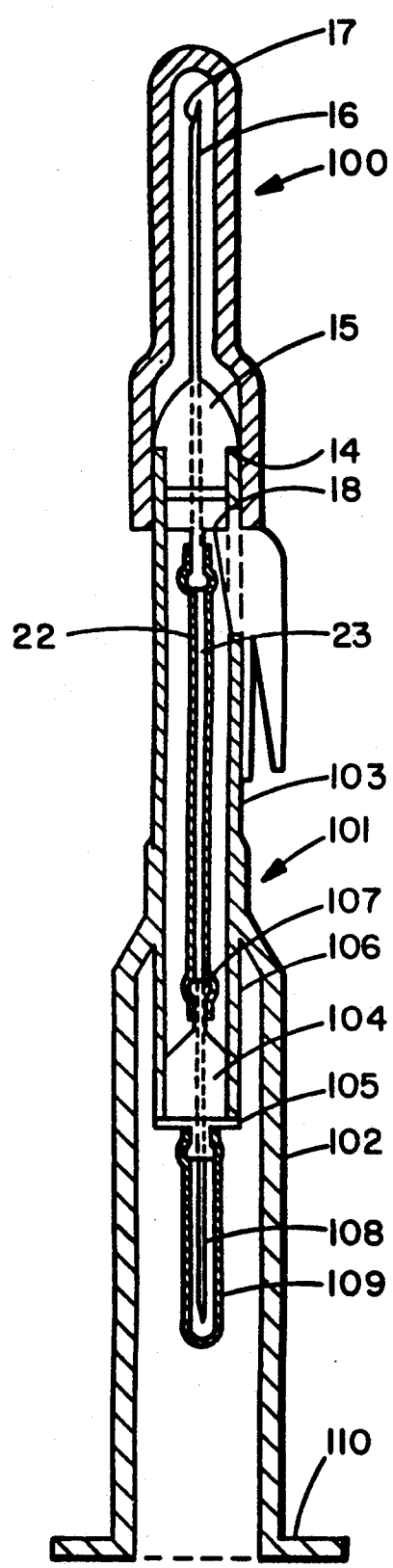
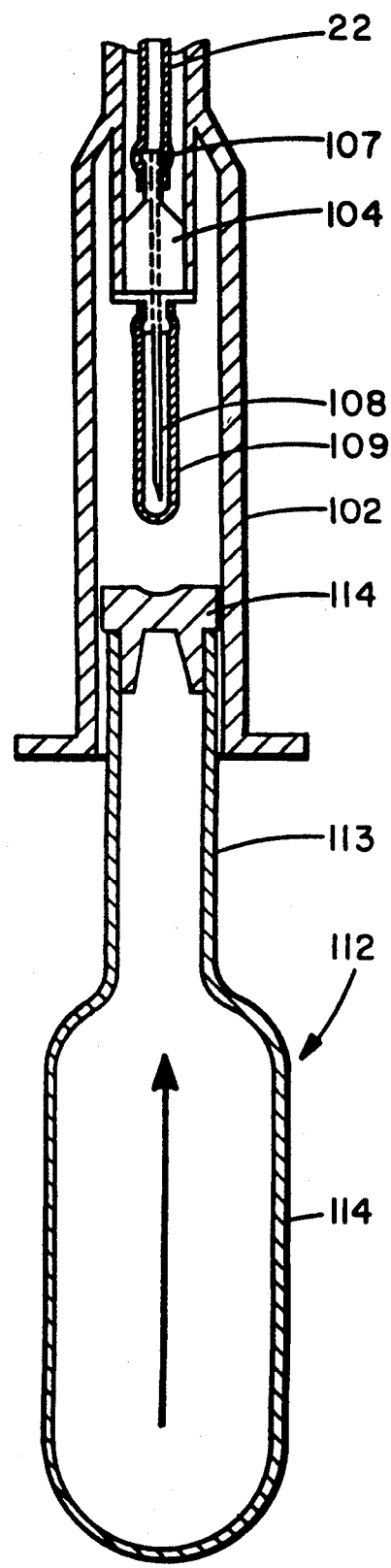
FIG 6a
FIG 6b

HYPODERMIC NEEDLE

FIELD OF THE INVENTION

This invention relates to hypodermic needle assemblies in which, after use in a medical procedure on a patient, the needle or cannula may be retracted into a barrel or housing so as to prevent it from causing an accidental scrape or puncture wound to medical personnel or others.

BACKGROUND OF THE INVENTION

It is very common practice in treating a patient that a hypodermic needle may be utilized either to draw blood or to inject a substance into a patient. A danger is involved here if, after puncturing the patient with a needle either for drawing blood or introducing a substance to the patient, the needle continues to be exposed and presents a safety hazard.

Accidental injury with a used hypodermic or phlebotomy needle is not uncommon with health care workers including nurses, physicians, laboratory workers, and housekeeping personnel. Such needle sticks or punctures can result in transmission of hepatitis and potentially the Acquired Immunodeficiency Syndrome, otherwise known as AIDS, and other transmittable diseases.

Accidental needle sticks or punctures can occur when a blood drawer attempts to recap a needle after use or leaves a contaminated needle exposed on a work surface where the blood drawer or other workers may accidentally impale themselves. This problem had previously been recognized and is described in various previous patent publications. For many years it was common practice merely to recap the needle after use with a protective shield.

In view of these known hazards with used hypodermic needles and syringes, various constructions of such syringes have been proposed to cover or occlude the cannula after use. For example, U.S. Pat. No. 4,874,383 discloses a syringe shield which can be drawn out over the needle and firmly locked into position to prevent accidental contact of the user with the needle.

U.S. Pat. No. 4,973,316 discloses a syringe in which the needle is retractable into a hollow barrel after use. The needle is subjected to the energy stored in a compressed spring; when the spring is permitted to expand, it will carry the needle into the tube.

U.S. Pat. No. 4,747,831 discloses a device in which the needle is spring-loaded and may be retracted in a tube or what may be described as a shell member so that after use on one patient it no longer presents the risk of puncture or scratching to the user. U.S. Pat. No. 3,314,428 also discloses a structure in which a needle is retracted within a sheath or tube after use.

Other U.S. patents as disclosed and discussed in the Information Disclosure Statement accompanying this application show other devices for retracting a hypodermic needle or cannula into a protective shell or region after use thereof either for drawing blood or intraveneous injection of fluids in which the needle is used for piercing a patient. These known hypodermic syringes are not easy to assemble, and in some cases, require the use of both hands in order to release the retraction mechanism to withdraw the needle from its position of use.

The present invention provides a new and improved hypodermic needle assembly in which after use the cannula may be withdrawn to an innocuous position where it is not possible to wound the user of the needle.

An object of this invention is to provide a new and improved hypodermic syringe with a retractable needle or cannula.

Another object of this invention is to provide a syringe with a retractable needle which is easily manipulated with one hand.

A further object of this invention is to provide a new and improved syringe with a retractable needle which is of simplified construction.

A still further object of this invention is to provide a retractable hypodermic needle assembly which can be coupled with or be made part of a unit designed to fill an evacuated collection vessel with blood (phlebotomy) or other body fluids. A still further object of this invention is to provide a retractable hypodermic needle assembly with a retraction mechanism which is both rapid and forceful enough to automatically pull the needle out of the puncture wound of the patient and do so virtually instantaneously.

SUMMARY OF THE INVENTION

Briefly stated, the invention in one form thereof, comprises a needle assembly in which the cannula extends through a support member or nosepiece in an extended position. In a first embodiment the support member extends into a barrel or tube. Secured to the distal end of the needle is an elastomeric tube which is in tension and has its other end attached to a conventional luer lock ferrule at the other end of the tube. Means are provided on the tube for acting on the support member for holding the needle in an extended position. When in an extended position and prior to use the needle is covered by a sheath or protective shield. A trip lever is bonded to the tube and extends through a slot therein so as to engage the nosepiece and maintain the cannula extended by acting on the block which is fast on the needle adjacent the distal end thereof. When the trip lever, which is resilient, is actuated it is moved out of contact with the cannula block and the tensioned elastomeric tube immediately snaps the needle through the support member and into the protective outer tube. This needle assembly is adapted to be attached by the conventional luer lock to a syringe. The elastomeric tube acts as a return spring and also as a conduit for injecting fluid into the body or for drawing blood if used as a phlebotomy needle.

In another embodiment of the invention the needle is held in an extended position by resilient jaw-like members bearing on the cannula. A jaw-release sleeve is disposed around the barrel. When the jaw-release sleeve is moved axially of the barrel, it will release the jaws from engagement with the cannula and permit the elastomeric tube to withdraw the cannula into the barrel. The distal end of the elastomeric tube may be attached to a luer lock ferrule for direct attachment to a syringe for injection use or may terminate in a piercing needle which is commonly used for vacuum phlebotomy blood collection or alternatively may terminate in a plastic tube which is connected to an intravenous infusion assembly.

The features of the invention which are believed to be novel are particularly pointed out and distinctly claimed in the concluding portion of this specification. However, the invention together with further objects and advantages thereof may best be appreciated by reference to the following detailed description taken in conjunction with the drawings.

BRIEF DESCRIPTION OF THE DRAWINGS

FIG. 2a is a longitudinal, half-section view of another needle assembly embodying the invention;

FIG. 2b is a longitudinal, half-section view of the device of FIG. 2, with the cannula of the needle assembly in a retracted position;

FIG. 4a is a longitudinal half-section of a complete disposable hypodermic syringe system embodying the invention; and FIG. 4b is an enlarged view of a portion of FIG. 4a.

FIG. 6a is a longitudinal elevation in half section of another phlebotomy needle assembly embodying the invention; and FIG. 6b is an enlarged view of a portion of FIG.6a with the addition of a vacuum collection vessel.

DETAILED DESCRIPTION OF PREFERRED EMBODIMENTS OF THE INVENTION

Figure 1A:
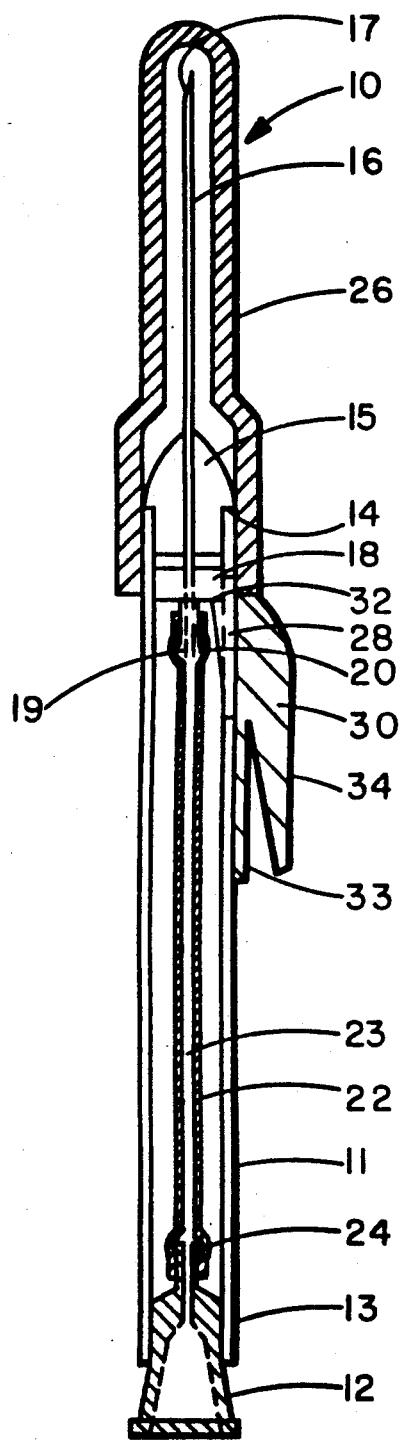
FIG. 1a is a longitudinal elevation in half-section of a needle assembly embodying the invention.
Figure 1B:
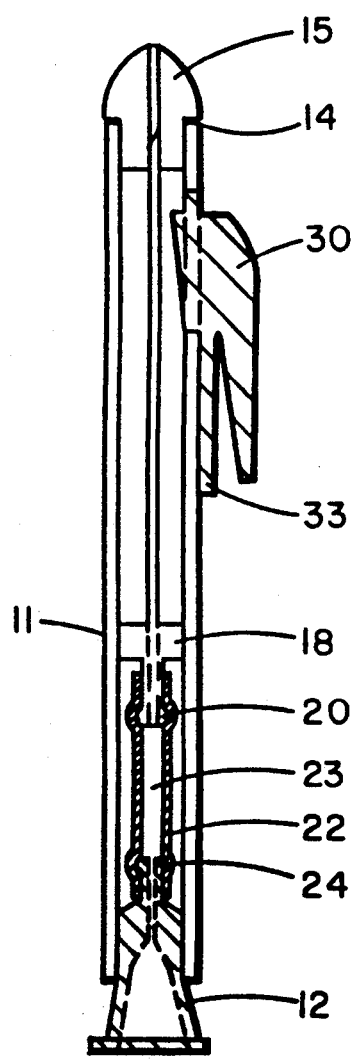
FIG. 1b is a longitudinal, half-section view of the assembly of FIG. 1, but showing the cannula of the needle assembly in a retracted position.

Reference is now made to FIGS. 1a and 1b which disclose a needle assembly 10 which comprises a tubular barrel member 11 receiving a conventional luer lock ferrule 12 at end 13 thereof. While it is preferred to use a luer lock ferrule, other connection devices may be utilized for attachment of a syringe assembly to the needle assembly 10. The term syringe assembly is intended to define a cylindrical tube with a moveable piston plunger therein which may be utilized either to create a vacuum and draw blood or to inject a fluid into a body. At the other end of barrel 11 there is defined an upper shoulder 14 which receives thereon what may be termed a nose or support piece 15 through which a cannula 16 extends, the cannula having the usual bevelled end 17. The cannula is axially moveable through nosepiece 15, but has a block member 18 affixed thereto.

Extending between the distal end 19 of cannula 16 and a fitting 20 on the end of block member 18 is an elastomeric tube 22 which defines a passage 23 therethrough. This passage is continuous with the passage through cannula 16 and the passage in the luer lock fitting 12. The elastomeric tube 22 is bonded to a fitting 20 on the end of cannula 16 and also to fitting 24 on the luer lock ferrule 12. Thus the elastomeric tube 22 provides a dual function in providing a passage for fluid from the point 17 of cannula 16 to the luer lock ferrule 12, and also serving as a cannula retraction device.

As previously described, the term "luer lock" is used here to define a preferable fitting which is conventionally used in medical practice and is used to mate the needle assembly 10 to a syringe assembly. However, the luer lock fitting may be replaced by other fittings either to receive a syringe having a compatible fitting, or to connect the needle assembly 10 to phlebotomy or intraveneous infusion devices.

As used herein, the term "cannula" refers to the actual device which may be called a needle or puncturing device as may be manufactured by a process as shown in U.S. Pat. No. 4,173,100, and comprises only the puncturing tube.

The term "needle assembly" is intended to identify the assembly including the cannula as shown in the various Figures and descriptions of the invention which assembly is to be attached to a syringe which in essence comprises a piston and cylinder which may be used either for evacuation or injection purposes.

The term "hypodermic syringe" is intended to identify a complete assembly of a needle assembly and a syringe.

The term "phlebotomy" or "phlebotomy needle" refers to a needle assembly for drawing blood from a patient.

The term "syringe" is intended to mean a plunger or piston assembly which is attached to a needle assembly to form a hypodermic syringe as defined above.

Prior to use, a protective shield 26 is place over the forward end of barrel 11 to protect against any inadvertent puncture or scraping wounds.

Barrel 11 has defined therein an opening 28 which receives therein a portion of a trip lever 30. It will be noted the trip lever 30 has a shoulder 32 thereon which holds block 18 in a position which tensions elastomeric tube 22. The trip lever 30 has a portion 33 which is glued or otherwise adhered to the outside surface of barrel 11. After use of the needle assembly, either for injection or blood drawing purposes, the handle 34 of trip lever 30 may be depressed to withdraw the shoulder 32 from a holding position with respect to block 18.

At that time, with no restraint, the elastomeric tube 22 will draw the cannula 16 downwardly through nosepiece 15 into barrel 11 and will then occlude or conceal the point 17 of cannula 16. As previously stated, a slot identified by the reference numeral 28 is defined in the wall of barrel 11 to permit shoulder portion 28 of release lever 30 to hold block 18 from retraction due to the energy stored in elastomeric tube 22.

In an alternate design of this embodiment, the nosepiece 15 together with blocking member 18 could be made integral and both be made fast to cannula 16. In this case the nosepiece 15 would not rest on the shoulder 14 of barrel 11 but the nosepiece 15 would be retractable within barrel 11.

Figure 2C:
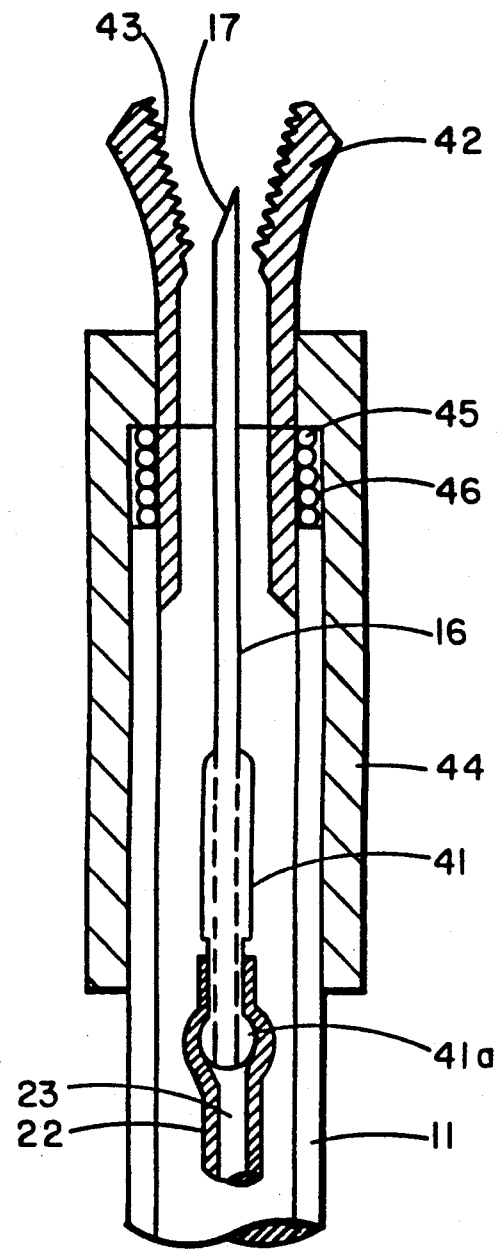
FIG. 2c is an enlarged half-section view of a portion shown in both FIGS. 2a and 2b.

It is emphasized that nosepiece 15 as shown in primarily provided for stability of cannula 16. Reference is now made to FIGS. 2a, 2b, and 2c which disclose a hypodermic needle assembly 40 in which a different type of holding and release device is utilized to maintain the needle in an extended position and permit retraction thereof after use. The reference numerals in FIGS. 2a, 2b, and 2c correspond to similar parts of those utilized in conjunction with FIGS. 1a and 1b.

In addition to the parts previously described, a plastic sleeve 41 is fast on cannula 16, and, when the cannula is in the operative position, is engaged by jaws 42 having serrations 43 thereon, as more clearly shown in FIG. 2c. The jaws may be formed by molding them as part of barrel 11 in one piece of a resilient plastic material. The jaws, in a position to hold cannula 16 operative, are engaged by a jaw release sleeve 44 which has an undercut shoulder 45 thereon, as most clearly shown in FIG. 2c. Disposed between the end 14 of barrel 11 and shoulders 45 is a spring 46. In the operative position of the cannula 16, the spring 46 is extended, and acting on the shoulders 45 of jaw sleeve 44, holds the jaws 42 in contact with sleeve 41. In this position the elastomeric tube 22 is held in an extended position, and the cannula extends into protective shield 26. The sleeve 41 has a head or fitting 41a thereon over which is fitted end 22a of elastomeric tube 22. The other end 22b of elastomeric tube 22 is fitted over fitting 25 on luer lock ferrule 12. In operation, the protective shield 26 is removed at the time of or subsequent to attachment of luer lock ferrule 12 to a syringe. The resulting hypodermic syringe then may either be loaded with a fluid for injection or may be utilized for drawing of blood. Upon removal of the cannula from the patient and ejection of the blood (if used for phlebotomy), the jaw closing sleeve 44 is moved downwardly (as shown in FIG. 2c which compresses spring 46 and permits the jaws 42 to open and disengage from sleeve 41. When this occurs, the jaws will release the cannula 16, and the elastomeric tube 22 will retract it within barrel 11. Releasing sleeve 44 now allows spring 46 to move it upwardly to beyond jaws 42 as shown in FIG. 2b.

Figure 3:
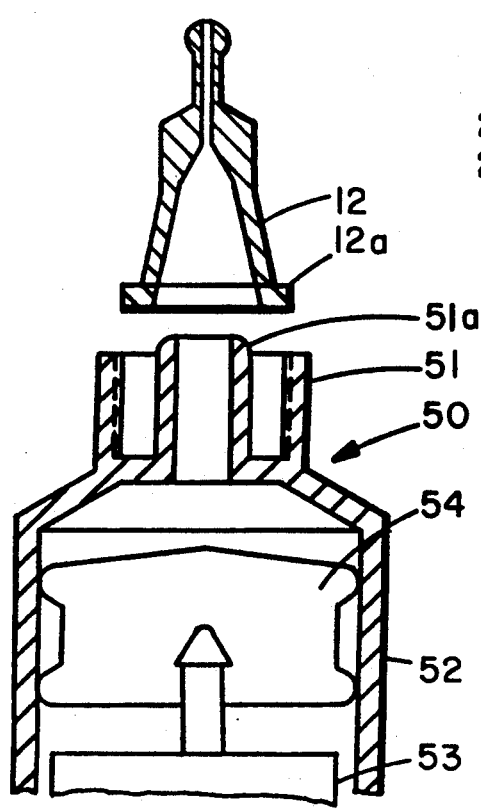
FIG. 3 is a fragmentary view of the mating of a hypodermic syringe and a needle assembly.

For purposes of illustration and disclosure, FIG. 3 exemplifies a syringe 50 adapted to be fitted to the luer lock ferrule 12 and comprises a nose portion 51 which is an extension of a cylinder 52 and includes a nozzle portion 51a. The nose portion 51 has threads which receive ears 12a of luer lock ferrule 12 and form a seal therewith. In many cases, the needle assembly and the syringe are stored separately and are only assembled when a hypodermic syringe is to be formed and used. Within the cylinder 52, a plunger shaft 53 carries an elastomeric piston 54 thereon which forms seals with internal walls of cylinder 52. Upon retraction shaft 53 and piston 54 will create a lessened atmospheric pressure of vacuum within cylinder 52, and upon forward movement, that is, towards the ferrule 12, will expel any liquid in the cylinder through elastomeric tube 22 and cannula 16. The joining of a syringe with a needle assembly are conventional and need not further be described. Other fittings as between a needle assembly and a syringe other than a luer lock may be utilized as is well known in the art.

A complete hypodermic syringe may be provided which utilizes the invention.

Reference is now made to FIGS. 4a and 4b which disclose a complete hypodermic syringe 60 embodying the invention. FIG. 4b is an enlarged view of a portion of FIG. 4a. The similar parts in FIGS. 4a and 4b to those shown in FIGS. 1a, 1b, and 2a-2c bear the same reference numerals. The syringe portion comprises a barrel 62 having a plunger 63 therein. The barrel portion includes finger grips 64 for underlying of the fingers thereon. The plunger 63 carries one or more O-ring seals 65 at the forward end thereof. Received within the plunger 63 is a jaw release rod 66 which receives an O-ring seal 67, which is in a sealing engagement within the side wall of plunger 63. Jaw release rod 67 has a fitting 68 extending therefrom which is engaged by an end of tube 22. The cylinder 62 has an extension 62a thereon of smaller dimensions, which provides a similar function to sleeve 44 of FIGS. 2a-2c.

A jaw tube 69 extends substantially the length of cylinder 62 and has a relieved portion 70 within cylinder portion 62a in which a spring 71 is disposed between a shoulder 72 on cylinder portion 62a and rests on an O-ring 72 on a shoulder 73 on jaw release sleeve 69. To draw fluid into the cylinder the protective shield 26 is removed and the cannula 26 is inserted into the source of fluid, which may be a vial or may be a body vein. When the plunger 63 is retracted, fluid will flow into and through cannula 16 through the passage 23 defined in tube 22 into a passage 75 in jaw release rod 66 through lateral passages 76 through the space 77 defined between jaw tube 68 and plunger 63 into the area 78 of cylinder 62 as most clearly seen in FIG. 4b.

The fluid in cylinder 62 may now be either utilized for injection or ejected for testing in the case of phlebotomy. After injection of fluid by the hypodermic syringe the jaw release rod is activated by pressing on a plug 79 in the end thereof. As jaw release rod 66 moves forward it will move the jaw 42 outwardly of cylinder 62 and release the fitting member 41. At this point the elastomeric tube 22 will quickly retract the cannula 16 within cylinder 62a.

Again the cannula is safely enclosed within the mechanism with the tip 17 withdrawn.

Figure 5A:
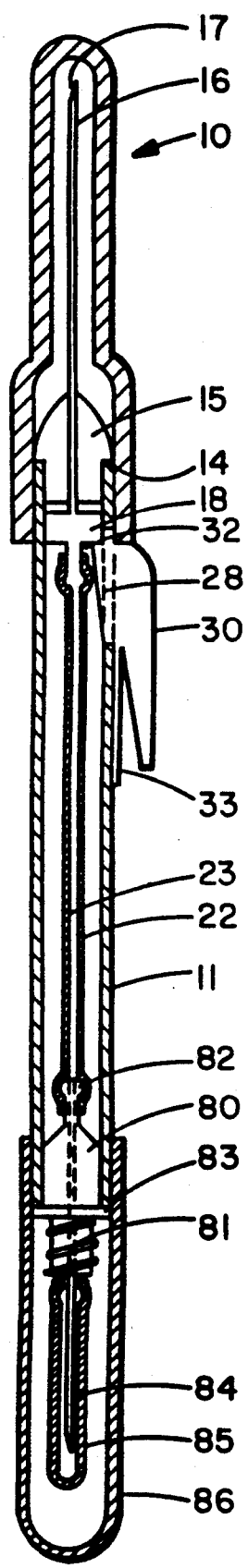
FIG. 5a is longitudinal elevation in half section of a phlebotomy needle embodying the invention.
Figure 5B:
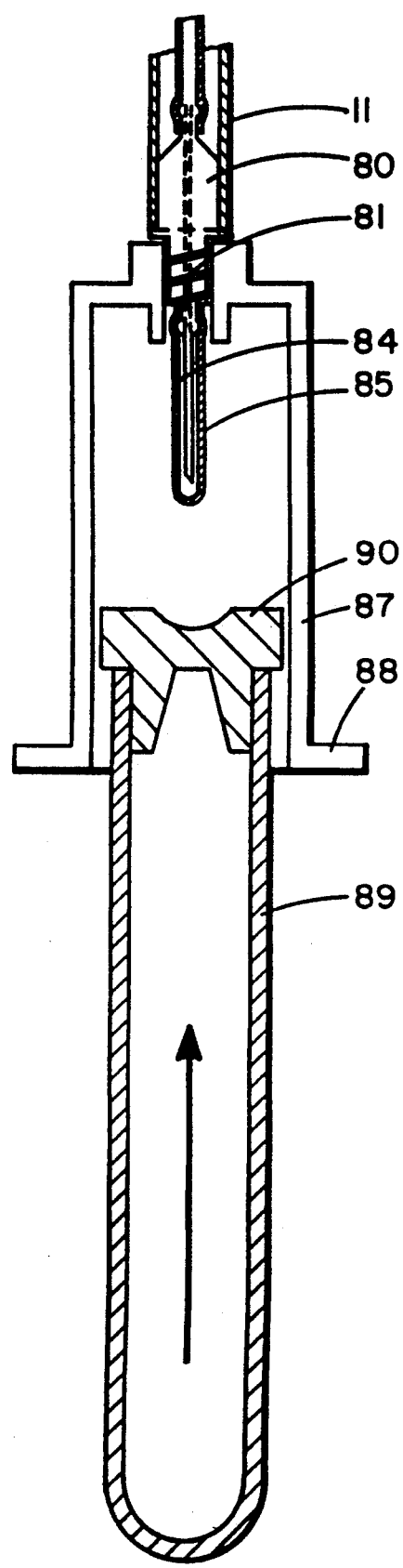
FIG. 5b is an enlarged view of a portion of FIG. 5a and additionally shows the addition of a vacuum guide barrel and an evacuated collection vessel.

FIGS. 5a and 5b exemplify a needle assembly for the drawing of blood, otherwise known as a phelobotomy needle. In FIG. 5, reference numerals designating the same elements as shown in FIG. 1 are repeated.

As shown in FIG. 5a, the tube 22 is connected to a fitting 80 which has a screw connector, 81. The fitting 80 also has an adapter 82 arranged to receive the distal end of tube 22. Extending from fitting 83 is a piercing needle 84 which is enclosed in a rubber or other elastomeric sheath, 85. A protective shield, 86, is received along barrel 11 to guard against accidental puncture by needle 84.

Reference is now made to FIG. 5b, which shows a fragmentary view of the needle assembly of FIG. 5a, and a guide barrel and an evacuated collection vessel. The guide barrel 87 is threaded to mate with the screw connector 81 and is adapted to receive an evacuated collection vessel 89, which is closed with a piercable rubber stopper 90. The guide barrel 87 serves to guide the piercing needle 84 to the thinnest portion of the rubber stopper 90 for easier penetration.

As previously stated, this arrangement is especially adapted for blood collection (phlebotomy), or the aspiration of other body fluids, and the collection vessel 89 is at less than atmospheric pressure. The use of such vacuum collection vessels or vials is well known. In operation, the needle 16 is inserted into the patient; the collection vessel is moved upwards (as shown in FIG. 5b) and the stopper will be punctured by the piercing needle 84. At this time, the covering 85 of the needle 84 will also be punctured and collapsed on itself as the piercing needle moves through the stopper 90. When the needle 16 is in a vein or artery, and the piercing needle 84 has entered into collection vessel 89, blood will flow from the patient into the collection vessel until the vacuum in it is satisfied.

When the filled collection vessel 89 is withdrawn from the guide barrel 87, the protective sheath 85 which had previously been moved upwardly over needle 84 will return through its elastic memory to cover the end of the piercing needle 84, and thus seal off the fluid path and prevent leakage of blood. A new evacuated collection vessel can now be inserted into guide barrel 87 and the procedure is repeated until sufficient blood for the various tests has been drawn. The volume of the collection vessels used varies, depending on the test to be performed and in many cases contains additives which have been pre-charged into the collection vessel, depending upon the test for which they are intended. After the necessary collection vessels have been filled and removed, the trip lever 30 is actuated and the cannula 16 pulls out of the puncture in the patient and retracts into barrel 11 as previously described in conjunction with FIG. 1.

FIGS. 6a and 6b illustrate another embodiment of the invention useful in phlebotomy. Like parts to those shown in FIG. 1 bear the same reference numerals.

The embodiment of FIGS. 6a and 6b is essentially the same as FIGS. 5 and 5a except that:

a) The guide barrel is molded or machined in one piece as part of the needle assembly barrel 11 shown in previous examples of the invention. This avoids the need of assembling the guide barrel to the needle assembly barrel via the screw connection 81 shown in FIGS. 5a and 5b. After use it is discarded together with the rest of the device.

b) the diameter of the guide barrel is reduced to ½" or less to avoid the risk of insertion of a finger.

c) To accommodate the smaller diameter of (b) above, the evacuated collection vessel has a neck portion small enough to fit into the reduced size guide barrel. To accommodate various volumes of fluid to be drawn, the bulbous portion of the vessel is varied to contain the volume desired.

In FIG. 6a the cannula 16 with point 17 extends through a guide member 15, and has affixed thereto the block member 18. The guide member 15 rests on shoulders 14 of a barrel member generally indicated by the reference numeral 101. Barrel member 101 is cast or moulded with a guide barrel 102 and a tubular sleeve or second barrel 103, which provides the shoulders 14. As previously described, the cannula 16 has its distal end connected to an elastomeric tube 22, which provides a through passage 23. The distal end of tube 22 is connected to a fitting indicated by the reference numeral 104, having a flange 105 thereon which is received on the end of an integral tube 106 extending from sleeve 103 into guide barrel 102. Fitting 104 also has an adapter member 107 thereon which receives the distal end of tube 22. Fitting 104 also receives a piercing needle 108 which extends therethrough and communicates with tube 22. Disposed about piercing needle 108 is a rubber or other elastomeric sheath 109 which serves the same function as previously described by the sheath 85 in FIGS. 5a and 5b. The guide barrel 102 also has a finger-grip flange 110 thereon.

In accordance with another aspect of the invention, the guide barrel is made in a dimension that is sufficiently small to prohibit insertion of a finger therein, which may be pierced by the needle 108. A preferred inside diameter of guide barrel 102 is one-half inch or less; there also should be three-quarters of an inch or more dimension between the tip of needle 108 and the finger flange 110.

Referring now to FIG. 6a, there is shown an evacuated collection vessel, 112, having a neck portion 113 with a piercable rubber stopper 114 received in the end of the neck.

In operation, when blood is to be drawn, and the cannula 16 is inserted into the vein or artery of the patient, collection vessel 114 is moved upwardly (as shown in FIG. 6b) so that the piercing needle 108 pierces stopper 114 and a passage is created from cannula 16, elastomeric tube 22, fitting 104, needle 108 and into vacuum vessel 114 to draw blood from the patient.

The invention provides a new and improved hypodermic needle assembly and a hypodermic syringe which provides easy retraction of a cannula into a safe position where the tip of the cannula is safely enclosed within a cylinder, barrel, or housing, as the terms may be utilized.

The invention further provides an easily assembled hypodermic needle assembly or a syringe in which the cannula may be extended and gripped in an operative position, and other efficient means are utilized so that after use of the hypodermic syringe or the needle assembly in conjunction with a syringe, whereby the cannula may be quickly retracted into a protective shell, barrel, or housing so that there is no danger to the user or other personnel of a medical laboratory as to scratching or puncture. The invention is also adapted for use in phlebotomy and intravenous infusion. As used herein, "hypodermic needle assembly" applies to all uses of the invention.

Devices embodying the invention are further beneficial in quickly and efficiently withdrawing a cannula from a patient by manipulating the trip lever on the jaw release sleeve.

It may thus be seen that the objects of the invention as stated above as well as those made apparent from the foregoing description are efficiently attained. While preferred embodiments of the invention have been set forth for purposes of disclosure, modification to the disclosed embodiments of the invention, as well as other embodiments thereof, may occur to those skilled in the art. Accordingly, the appended claims are intended to cover all embodiments of the invention and modifications to the disclosed embodiments of the invention which do not depart from the spirit and scope of the invention.

What is claimed is:

1. A hypodermic needle assembly comprising a tubular barrel member, a cannula extending from said barrel member, an elastomeric tube connected between said cannula and a fitting at the distal end of the barrel member providing a fluid passage therebetween, said tube being stressed along its length between said cannula and said fitting, releasable means holding said elastomeric tube in a stressed state and means for actuating said releasable means whereby said elastomeric tube retracts said cannula within said barrel.

2. The assembly of claim 1 wherein said cannula has a block member fast thereon, and said releasable means engages said block member to hold said cannula in an operative position.

3. The assembly of claim 2 wherein said releasable means is accessible from outside of said barrel member.

4. The assembly of claim 3 wherein said releasable means extends into said barrel.

5. The assembly of claim 1 wherein said releasable means comprises gripping means disposed at least partially within said barrel and engaging said cannula, and said actuating means release said gripping means to permit said tube to retract said cannula.

6. The assembly of claim 5 wherein said actuating means comprise a sleeve disposed about said barrel.

7. The assembly of claim 6 wherein said gripping means comprise a plurality of angularly arranged jaws grasping said cannula, said actuating means holds said jaws in contact with said cannula to hold said cannula in an operative position, said sleeve being axially movable on said barrel so as to release said jaws and permit said tube to retract said cannula.

8. The assembly of claim 1 wherein said releasable means comprise a plurality of flexible jaws engaging said cannula, and means for activating said releasable means from engagement with said cannula.

9. The assembly of claim 1 wherein said releasable means comprises means engaging said cannula to prevent retraction thereof, and means external to said barrel for activating said releasable means to permit said tube to retract said cannula.

10. The assembly of claim 5 wherein said cannula at the distal end receives a fitting fast thereon, said fitting comprising a cylindrical portion adapted to be engaged by said gripping means and a head portion receiving an end of said tube.

11. The assembly of claim 10 wherein said needle assembly includes a syringe fitting with a head thereon adapted to receive the other end of said tube.

12. The assembly of claim 11 wherein said gripping means grip said fitting on said cannula.

13. A hypodermic syringe comprising a barrel member, a plunger member slideably received within said barrel member, a cannula extending from said barrel member, holding means at least partially within said barrel member holding said cannula in an extended position, an elastomeric tube within said barrel member connected to said cannula at one end thereof, holding means within and extending axially of said plunger, and holding said cannula in an extended position, a release member in contact with said holding means, said tube being longitudinally stressed between said cannula and said release member and defines a passage therethrough from said cannula, passages defined in said release member to said barrel member whereby a fluid may be accepted in said barrel member as said plunger is withdrawn from said barrel member, said release member being effective to release said holding means and permit said elastomeric tube to retract said cannula into said barrel.

14. The syringe of claim 13 wherein said holding means comprises a tubular member within said plunger having jaws holding said cannula in an extended position, means within said barrel biasing said tubular member into said barrel and maintaining said jaws in contact with said cannula, said release member arranged to transmit an axial force to said tubular member to overcome said biasing means and allow said jaws to release said cannula.

15. The syringe of claim 13 wherein a fitting is disposed fast on said cannula at the distal end thereof and said tube is connected thereto.

16. The syringe of claim 15 wherein said jaws grasp said fitting to hold said cannula in an extended position.

17. The syringe of claim 13 wherein said release member has a fitting thereon receiving an end of said tube.

18. The syringe of claim 17 where said tube extends between said cannula and the fitting on said release member.

19. A hypodermic needle assembly comprising a tubular barrel member, a cannula extending from said barrel member, an elastomeric tube connected between said cannula and a fitting of the distal end of the barrel member providing a fluid passage there between, said tube being stressed in an extended state long its length between said cannula and said fitting, releasable means holding said elastomeric tube in a stressed state and means for actuating said releasable means, whereby said elastomeric tube retracts said cannula within said barrel and a needle extending from said fitting away from said cannula.

20. The needle assembly of claim 19 where said needle is adapted to puncture a stopper of a vacuum vial.

21. The needle assembly of claim 20 wherein said needle adapted to puncture is enclosed within an elastomeric sheath.

22. The needle assembly of claim 21 further including a guide barrel connected to said fitting, said guide barrel receiving a vacuum vial therein having a stopper therein adapted to be pierced by said needle whereby fluid may be drawn through said cannula into said evacuated vessel.

23. The needle assembly of claim 19, wherein a guide barrel for a vacuum vial is formed integral with said barrel member, said guide barrel extending beyond said needle and having an inside diameter of a size to inhibit insertion of a finger therein.

24. The needle assembly of claim 23 further including a vacuum vial having a neck portion and a body portion, said body portion being of a greater diameter than said neck portion, said neck portion having a puncturable elastomeric stopper thereon adapted to be punctured by said needle upon insertion of said neck portion into said guide barrel.

* * * * *